United States Patent
Deren-Lewis et al.

(10) Patent No.: US 11,033,568 B2
(45) Date of Patent: Jun. 15, 2021

(54) NICOTINAMIDE RIBOSIDE COMPOSITIONS FOR TOPICAL USE IN TREATING SKIN CONDITIONS

(71) Applicant: ChromaDex Inc., Irvine, CA (US)

(72) Inventors: Ann Deren-Lewis, Irvine, CA (US); Troy Rhonemus, Irvine, CA (US)

(73) Assignee: ChromaDex Inc., Irvine, CA (US)

( * ) Notice: Subject to any disclaimer, the term of this patent is extended or adjusted under 35 U.S.C. 154(b) by 0 days.

(21) Appl. No.: 16/891,824

(22) Filed: Jun. 3, 2020

(65) Prior Publication Data
US 2020/0289536 A1    Sep. 17, 2020

Related U.S. Application Data

(62) Division of application No. 15/033,285, filed as application No. PCT/US2014/063260 on Oct. 30, 2014, now Pat. No. 10,688,118.

(60) Provisional application No. 61/897,713, filed on Oct. 30, 2013.

(51) Int. Cl.
*A61K 31/706* (2006.01)

(52) U.S. Cl.
CPC .................. *A61K 31/706* (2013.01)

(58) Field of Classification Search
None
See application file for complete search history.

(56) References Cited

U.S. PATENT DOCUMENTS

| | | | |
|---|---|---|---|
| 7,776,326 B2 | 8/2010 | Milbrandt et al. | |
| 7,977,049 B2 | 7/2011 | Sinclair et al. | |
| 8,197,807 B2 | 6/2012 | Brenner | |
| 2006/0229265 A1 | 10/2006 | Milburn et al. | |
| 2008/0194803 A1 | 8/2008 | Sinclair et al. | |
| 2009/0069444 A1 | 3/2009 | Joseph et al. | |
| 2012/0172584 A1* | 7/2012 | Sauve ................ | A61K 31/706 536/28.1 |

FOREIGN PATENT DOCUMENTS

| | | |
|---|---|---|
| JP | 2008-529502 A | 8/2008 |
| WO | 2006/086454 A2 | 8/2006 |

OTHER PUBLICATIONS

Applegate, L A, et al., Identification of the Molecular Target for the Suppression of Contact Hypersensitivity by Ultraviolet Radiation. J Exp Med. Oct. 1, 1989;170(4):1117-31.

Berge, S., et al., Pharmaceutical Salts. J Pharm Sci. Jan. 1977;66(1):1-19.

Haratake, A., et al., UVB-induced alterations in permeability barrier function: roles for epidermal hyperproliferation and thymocyte-mediated response. J Invest Dermatol. May 1997;108(5):769-75.

Jiang, S.J., et al, Ultraviolet B-induced alterations of the skin barrier and epidermal calcium gradient. Exp Dermatol. Dec. 2007;16(12):985-92.

Surjana, D., et al., Role of Nicotinamide in DNA Damage, Mutagenesis, and DNA Repair. J Nucleic Acids. Jul. 25, 2010;2010.

Oba, C., et al., Collagen hydrolysate intake improves the loss of epidermal barrier function and skin elasticity induced by UVB irradiation in hairless mice. Photodermatol Photoimmunol Photomed. Aug. 2013;29(4):204-11. Abstract Only.

Ansel's Pharmaceutical Dosage Forms and Drug Delivery Systems, 9th Ed., L.V. Allen, Jr., Ed. (Philadelphia, Penn.: Lippincott Williams & Wilkins, 2011) pp. 272-293.

Devita Surjana. et al., "Nicotinamide enhances repair of ultraviolet radiation-induced DNA damage in human Keratinocytes and ex vivo skin", Carcinogenesis, Jan. 24, 2013, vol. 34, No. 5, 1144-1149.

Brigitte Balard and Paolo U. Giacomoni, "Nicotinamide adenosine dinucleotide level in demethylsulfate-treated or UV-irradiated mouse epidermis", Mutation Research, 1989, vol. 219, 71-79.

Federico Licastro and Roy L. Walford, "Modulatory Effect of Nicotinamide on Unscheduled DNA Synthesis in Lymphocytes From Young and Old Mice", Mechanisms of Aging and Development, 1986, vol. 35, 123-131.

H. A. Rovito and J. E. Oblong, "Nicotinamide preferentially protects glycolysis in dermal fibroblasts under oxidative stress conditions", British Journal of Dermatology, Mar. 4, 2013, vol. 169, Suppl. 2, 15-24.

Nobumasa Hara. Et al., "Nicotinic acid elevattes cellular NAD levels and protects cells against oxidative stress", Biochemistry, 2007, 1 P-02697.

(Continued)

*Primary Examiner* — Traviss C McIntosh, III
(74) *Attorney, Agent, or Firm* — Amin Talati Wasserman LLP; George M. Carrera, Jr.; Jonathan J. Krit

(57) ABSTRACT

Compositions containing nicotinamide riboside (NR) are provided. NR containing compositions are used in the care or treatment of skin and skin conditions. In some embodiments, the invention relates to pharmaceutical compositions and cosmetic compositions containing nicotinamide riboside. In further embodiments, the invention relates to methods of using nicotinamide riboside to promote the increase of intracellular levels of nicotinamide adenine dinucleotide (NAD+) in cells and tissues for improving cell and tissue survival. A method of treating signs or symptoms of aging or skin wrinkles in an individual is provided, comprising topically administering to the individual in need of such treatment an effective amount of the compound nicotinamide riboside, or salts thereof.

16 Claims, 6 Drawing Sheets

(56) References Cited

OTHER PUBLICATIONS

Alessandra Mocali. Et al., "Induction, Effects, and Quantification of Sublethal Oxiadtive Stress by Hydrogen Peroxide on Cultured Human Fibroblasts", Experimental Cell Research, 1995, vol. 216, 388-395.
Anthony A. Sauve, "Pharmaceutical Strategies for Activating Sirtuins", Current Pharmaceutical Design, 2009, vol. 15, 45-56.

* cited by examiner

\*\*\* p<0.001 compared to 1mM H2O2 alone (One Way ANOVA followed by Tukey's multiple comparison test)
\*p<0.05 compared to 1mM H2O2 alone (unpaired t-test)

+H2O2 lanes (left to right): 1 mM H2O2 (only); +0.04 mM NR (grey);

+0.2 mM NR (small checker)

+1 mM NR (large checker)

% protection compared to UV exposed control shown over bars

NICOTINAMIDE RIBOSIDE COMPOSITIONS FOR TOPICAL USE IN TREATING SKIN CONDITIONS

This application is a Divisional of U.S. patent application Ser. No. 15/033,285, filed on Apr. 29, 2016, which is a U.S. National Stage application under 35 U.S.C. § 371 of International Application No. PCT/US2014/063260, filed on Oct. 30, 2014, which claims the benefit of earlier filed U.S. Provisional Application No. 61/897,713, filed on Oct. 30, 2013, each of which are hereby incorporated by reference herein.

FIELD OF THE INVENTION

Compositions containing nicotinamide riboside (NR) may be used in the care or treatment of skin and skin conditions. In some embodiments, the invention relates to pharmaceutical compositions and cosmetic compositions containing nicotinamide riboside. In further embodiments, the invention relates to methods of using nicotinamide riboside to promote the increase of intracellular levels of nicotinamide adenine dinucleotide (NAD+) in cells and tissues for improving cell and tissue survival and overall cell and tissue health.

BACKGROUND

Enzymes that use NAD+ play a part in the DNA repair process. Specifically, the poly(ADP-ribose) polymerases (PARPs), particularly PARP-1, are activated by DNA strand breaks and affect DNA repair. The PARPs consume NAD+ as an adenosine diphosphate ribose (ADPR) donor and synthesize poly(ADP-ribose) onto nuclear proteins such as histones and PARP itself. Although PARP activities facilitate DNA repair, overactivation of PARP can cause significant depletion of cellular NAD+, leading to cellular necrosis. The apparent sensitivity of NAD+ metabolism to genotoxicity has led to pharmacological investigations into the inhibition of PARP as a means to improve cell survival. Numerous reports have shown that PARP inhibition increases NAD+ concentrations in cells subject to genotoxicity, with a resulting decrease in cellular necrosis. Nevertheless, cell death from toxicity still occurs, presumably because cells are able to complete apoptotic pathways that are activated by genotoxicity. Thus, significant cell death is still a consequence of DNA/macromolecule damage, even with inhibition of PARP. This consequence suggests that improvement of NAD+ metabolism in genotoxicity can be partially effective in improving cell survival but that other players that modulate apoptotic sensitivity, such as sirtuins, may also play important roles in cell responses to genotoxins.

Physiological and biochemical mechanisms that determine the effects of chemical and radiation toxicity in tissues are complex, and evidence indicates that NAD+ metabolism is an important player in cell stress response pathways. For example, upregulation of NAD+ metabolism, via nicotinamide/nicotinic acid mononucleotide overexpression, has been shown to protect against neuron axonal degeneration, and nicotinamide used pharmacologically has been recently shown to provide neuron protection in a model of fetal alcohol syndrome and fetal ischemia. Such protective effects could be attributable to upregulated NAD+ biosynthesis, which increases the available NAD+ pool subject to depletion during genotoxic stress. This depletion of NAD+ is mediated by PARP enzymes, which are activated by DNA damage and can deplete cellular NAD+, leading to necrotic death. Another mechanism of enhanced cell protection that could act in concert with upregulated NAD+ biosynthesis is the activation of cell protection transcriptional programs regulated by sirtuin enzymes.

Examples of cell and tissue protection linked to NAD+ and sirtuins include the finding that SIRT1 is required for neuroprotection associated with trauma and genotoxicity. SIRT1 can also decrease microglia-dependent toxicity of amyloid-beta through reduced NFKB signaling. SIRT1 and increased NAD+ concentrations provide neuroprotection in a model of Alzheimer's disease. Sirtuins are NAD+-dependent enzymes that have protein deacetylase and ADP-ribosyltransferase activities that upregulate stress response pathways. Evidence indicates that SIRT1 is upregulated by calorie restriction and in humans could provide cells with protection against apoptosis via downregulation of p53 and Ku70 functions. In addition, SIRT1 upregulates FOXO-dependent transcription of proteins involved in reactive oxygen species (ROS) detoxification, such as MnSOD. The sirtuin SIRT6 has been shown to participate in DNA repair pathways and to help maintain genome stability. With respect to nicotinyl ribosides including nicotinamide riboside, various uses have been proposed as in U.S. Pat. No. 8,106,184, herein incorporated by reference.

UV-Mediated DNA Damage

Ultraviolet (UV) light plays an integral role in the development of numerous skin ailments ranging from aging to cancer. Considerable evidence spanning decades has conclusively demonstrated that UV radiation triggers multiple independent cellular responses. UV radiation is known to penetrate skin where it is absorbed by proteins, lipids and DNA, causing a series of events that result in progressive deterioration of the cellular structure and function of cells (Valacchi, et al., "Cutaneous responses to environmental stressors," *Ann. N. Y. Acad. Sci.* (2012) 1271: 75-81). DNA is the building block of life and its stability is of the utmost importance for the proper functioning of all living cells. UV radiation is one of the most powerful (and common) environmental factors that can cause a wide range of cellular disorders by inducing mutagenic and cytotoxic DNA lesions; most notably cyclobutane-pyrimidine dimers (CPDs) and 6-4 photoproducts (64 pps) (Narayanan, et al., "Ultraviolet radiation and skin cancer," *Int. J. Dermatol.* (2010) 49: 978-86). It is important to note that UV-mediated DNA damage is an early event in a plethora of proliferative cellular disorders. The two major types of UV-induced DNA damage are CPDs and 64pp (along with their Dewer isomers) (Sinha, R. P. and Hader, D. P., "UV-induced DNA damage and repair: a review," *Photochem. Photobiol. Sci.* (2002) 1: 225-36; and Rastogi, et al., "Molecular mechanisms of ultraviolet radiation-induced DNA damage and repair," *J. Nucleic Acids* (2010) 2010: 592980). These abundant DNA lesions, if unrepaired, can interfere with DNA replication and subsequently cause mutations in DNA. Thus, these lesions can be mutagenic (potentially leading to proliferative disorders) and/or can be cytotoxic (resulting in cell death). 64pp occur at about one third the frequency of CPDs, but are more mutagenic (Sinha & Hader, 2002). In one embodiment, prevention of these UV-mediated DNA adducts is paramount to guarding against the onset of several proliferative disorders, ranging from aging to cancer.

UV-Mediated Loss of Barrier Function

Maintaining a water-impermeable barrier between the organism and the environment is an essential function of skin. This barrier function serves to prevent dehydration; which can lead to death of the organism (Jiang, S. J., et al., "Ultraviolet B-induced alterations of the skin barrier and epidermal calcium gradient," *Exp. Dermatol.* (2007) 16: 985-992). UV light has been demonstrated to disrupt epidermal skin barrier function in a dose-dependent manner (Haratake, A., et al., "UVB-induced alterations in permeability barrier function: roles for epidermal hyperproliferation and thymocyte-mediated response" *J. Invest. Dermatol.* (1997) 108: 769-775; and prev. citation). Skin barrier dysfunction can be directly assessed by measuring Transepidermal Water Loss (TEWL), which is a measure of skin hydration (Oba, C., et al., "Collagen hydrolysate intake improves the loss of epidermal barrier function and skin elasticity induced by UVB irradiation in hairless mice," *Photodermatol. Photoimmunol. Photomed.* (2013) 29: 204-11; and prev. citations).

Therefore, it is hypothesized that a chemopreventative agent for several human skin disorders will be effective at inhibiting or preventing the direct UV-mediated loss of barrier function, DNA damage, or oxidative damage in helping to maintain healthy human skin.

If a way could be found to use nicotinamide riboside, or salts thereof, in a topical skin care composition in the maintenance of healthy human skin, this would represent a useful contribution to the art. Furthermore, if a way could be found to use nicotinamide riboside, or salts thereof, in a cosmetic or cosmeceutical composition in the maintenance of healthy human skin, this would also represent a useful contribution to the art.

SUMMARY OF THE INVENTION

A skin care composition includes nicotinamide riboside, or salts thereof, optionally in combination with a compound selected from stilbenoids (e.g., pterostilbene), curcumin, peptides, retinols, salicylic acid, benzoyl peroxide, vitamin C (L-ascorbic acid), anthocyanins, or combinations thereof.

In one embodiment, the nicotinamide riboside is a salt form selected from fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, or trifluoroacetate.

A method of treating signs or symptoms of aging or skin wrinkles in an individual is provided, comprising topically administering to the individual in need of such treatment an effective amount of the compound nicotinamide riboside, or salts thereof.

A chemoprotective method is provided for treating or preventing UV-mediated DNA damage in the skin of an individual comprising topically administering to the individual in need of such treatment a therapeutically effective amount of the compound nicotinamide riboside, or a salt thereof.

A cytoprotective method is provided for treating or preventing oxidative damage in the skin of an individual comprising topically administering to the individual in need of such treatment a therapeutically effective amount of the compound nicotinamide riboside, or a salt thereof.

A method for treating or repairing a wound in the skin of an individual is provided, comprising topically administering to the individual in need of such treatment a therapeutically effective amount of the compound nicotinamide riboside, or a salt thereof, wherein skin cells in the skin have increased motility and/or proliferation.

DETAILED DESCRIPTION

Figure 1:
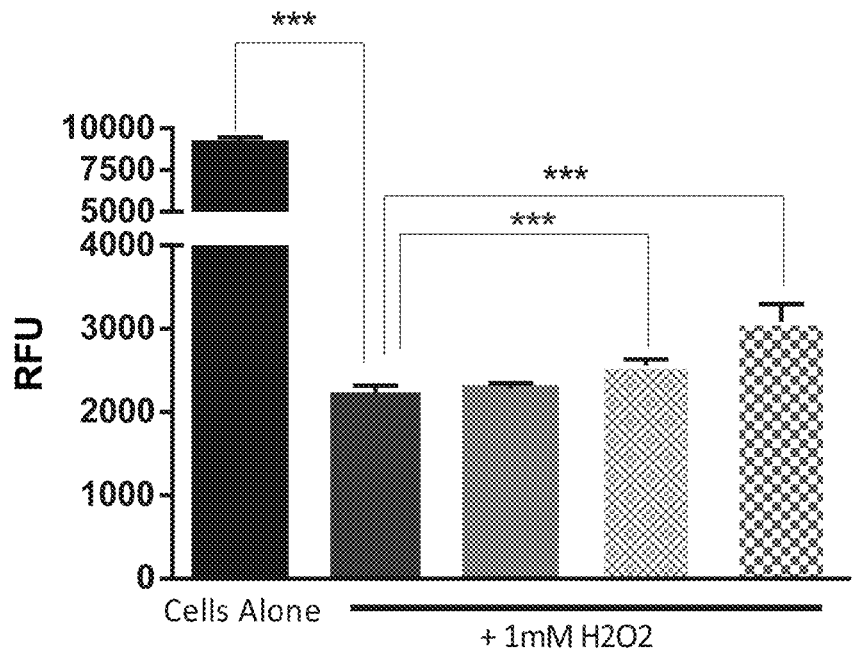
FIG. 1 depicts an oxidative damage protection assay of human epidermoid A431 cells incubated with 1 mM $H_2O_2$ under growth arrested conditions (1% fetal bovine serum, FBS); control, +0.2 mM NR; +1 mM NR; and +5 mM NR. Live cells are shown in reflective fluorescence units (RFU).

In certain embodiments, nicotinamide riboside (NR), or salts thereof, can increase NAD+ activity. It is also believed that increasing NAD+ activity can increase sirtuin activity because NAD+ can act as a substrate of SIRT1. Such agents can include NAD+ or NADH, a precursor of NAD+, an intermediate in the NAD+ salvage pathway or a substance that generates NAD+ such as a nicotinamide mononucleotide adenylyltransferase (NMNAT) or a nucleic acid encoding a nicotinamide mononucleotide adenylyltransferase. The nicotinamide mononucleotide adenylyltransferase can be an NMNAT1 protein. Other useful NAD+ precursors include nicotinamide and nicotinic acid. U.S. Pat. No. 7,776,326 to Milbrandt, et al., herein incorporated by reference discusses the NAD biosynthetic pathway.

In one embodiment, there is provided a method extending the lifespan of a cell, extending the proliferative capacity of a cell, slowing aging of a cell, promoting the survival of a cell, delaying cellular senescence in a cell, mimicking the effects of calorie restriction, increasing the resistance of a cell to stress, or preventing apoptosis of a cell, by contacting the cells with nicotinamide riboside, or salts thereof. In an exemplary embodiment, the methods comprise contacting skin cells with nicotinamide riboside, or salts thereof.

In another embodiment, cells that are intended to be preserved for long periods of time may be treated with nicotinamide riboside, or salts thereof. The cells may be in suspension (e.g., blood cells, serum, biological growth media, etc.) or in tissues or organs. For example, blood collected from an individual for purposes of transfusion may be treated with nicotinamide riboside, or salts thereof, to preserve the blood cells for longer periods of time. Additionally, blood to be used for forensic purposes may also be preserved using nicotinamide riboside, or salts thereof.

Particular cells that may be protected, or treated to extend their lifespan or protect against apoptosis with nicotinamide riboside, or salts thereof, include skin cells such as keratinocytes, melanocytes, dermal cells, epidermal cells, dendritic (Langerhans) cells, basal cells, squamous cells, stem cells, epidermal stem cells, hair follicles, and the like.

Other cells that may be treated to extend their lifespan or protect against apoptosis include cells for production, consumption, or food, e.g., cells from non-human mammals (such as meat) or plant cells (such as vegetables).

Nicotinamide riboside (NR) is a pyridinium compound having the formula (I):

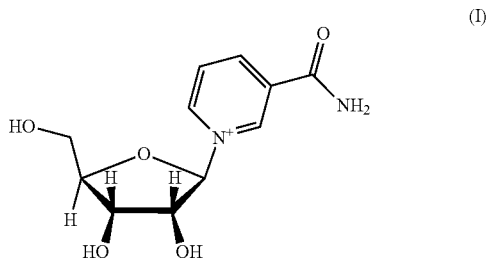

The compounds of formula (I) may include a salt counterion such as, but not limited to, halide (including chloride, bromide, iodide, and the like), formate, acetate, ascorbate, benzoate, carbonate, citrate, carbamate, formate, gluconate, lactate, methyl bromide, methyl sulfate, nitrate, phosphate, diphosphate, succinate, sulfate, trifluoroacetate, besylate, tosylate, triflate, mesylate, and the like. Reference is made to the latest edition of Remington's Pharmaceutical Sciences (Mack Publishing Co., Easton, Pa.), the article by S. Berge, et al., *J. Pharmaceut. Sci.* (1977) 66:1-19 (and references cited therein), and the book chapter by L. D. Bighley, et al., "Salt Forms of Drugs and Absorption," in *Encyclopedia of Pharmaceutical Technology*, J. Swarbrick, Ed., Vol. 13, pp. 453-499 (New York: Marcel Dekker, Inc., 1996) (and references cited therein); all incorporated by reference herein.

Nicotinamide riboside (NR), as a chloride salt, is commercially available as NIAGEN™ from ChromaDex Inc. (Irvine, Calif.).

Other useful compounds for topical application, alone or in combination with NR, include nicotinic acid riboside (NAR), 1,4-dihydro reduced NR or NAR (i.e., reduced nicotinamide riboside (NRH) or reduced nicotinic acid riboside (NARH)), and the like.

Nicotinamide riboside, or salts thereof, may also be applied during developmental and growth phases in mammals, plants, insects or microorganisms, in order to, e.g., alter, retard or accelerate the developmental and/or growth process.

A chemoprotective method for inhibiting or preventing DNA damage in skin caused by ultraviolet (UV) light, or inhibiting or preventing oxidative damage, by using an effective amount of NR has been discovered. Pharmaceutical and nutraceutical compositions containing pterostilbene suitable for administration to an individual in order to prevent subsequent UV-mediated DNA damage, or oxidative damage, in skin are described.

In another embodiment, nicotinamide riboside, or salts thereof, may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated with the nicotinamide riboside, or a salt thereof, prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with nicotinamide riboside, or salts thereof, or may have a subset of cells/tissue treated locally with nicotinamide riboside, or salts thereof. In certain embodiments, the cells or tissue (or donor/recipient individuals) may be treated with one or more additional therapeutic agents useful for prolonging graft survival, such as, for example, an immunosuppressive agent, a cytokine, an angiogenic factor, etc.

In yet other embodiments, cells may be treated with nicotinamide riboside, or salts thereof, that increases the level of NAD+ in vivo, e.g., to increase their lifespan or prevent apoptosis. For example, in a principal embodiment skin can be protected from aging (e.g., developing wrinkles, loss of elasticity, etc.) by treating skin or epithelial cells with nicotinamide riboside, or salts thereof, that increases the level intracellular NAD+. In an exemplary embodiment, skin is contacted with a pharmaceutical or cosmetic composition comprising nicotinamide riboside, or salts thereof, that increases the level of intracellular NAD+. Exemplary skin afflictions or skin conditions that may be treated in accordance with the methods described herein include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including pemfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, nicotinamide riboside, or salts thereof, that increase the level of intracellular NAD+ may be used for the treatment of wounds and/or burns to promote healing, including, for example, first-, second- or third-degree burns and/or thermal, chemical or electrical burns. The formulations may be administered topically, to the skin or mucosal tissue, as an ointment, lotion, cream, microemulsion, gel, solution or the like, as further described herein, within the context of a dosing regimen effective to bring about the desired result.

Topical formulations comprising one or more of nicotinamide riboside, or salts thereof, that increases the level of intracellular NAD+ may also be used as preventive, e.g., chemopreventive, compositions. When used in a chemopreventive method, susceptible skin is treated prior to any visible condition in a particular individual.

Topical formulations may include other NAD+ precursors, or compounds capable of increasing NAD+ in vivo, such as, but not limited to, nicotinamide and nicotinic acid.

Useful ranges of NR, or salts thereof, in the topical compositions include from about 0.001% to about 50% by weight, based on the total weight of the composition. Another suitable range for NR is from about 0.1% to about 10% by weight, based on the total weight of the composition. Another suitable range for NR is from about 0.5% to about 5% by weight, based on the total weight of the composition.

Oral formulations of NR are contemplated. Useful therapeutic dosages of NR can range, but are not limited to, from about 1 mg to about 5000 mg in a human individual. Another suitable dose range is from about 5 mg to about 500 mg. Another suitable dose range is from about 50 mg to about 500 mg. NR may be formulated orally or topically as a pharmaceutical or nutraceutical composition, including a pharmaceutically or nutraceutically acceptable carrier, respectively. In one embodiment of a pharmaceutical composition containing NR, a suitable level of NR may range from about 0.01% by weight to about 50% by weight, based on the total weight of the composition. In another embodiment of a pharmaceutical composition containing NR, a suitable level of NR may range from about 0.1% by weight to about 10% by weight, based on the total weight of the composition.

Human skin comprises a top epidermal layer (epidermis) which rests on a lower dermal layer (dermis). The epidermis is made up primarily of keratinocytes, which develop at the bottom, move toward the top, and are constantly replaced. As old dead cells are shed, they are replaced, so this layer is constantly renewing itself. The epidermis also contains melanocytes, located generally near the bottom of the layer, which produce the pigment melanin, contributing to skin color, and also providing UV-protection. The epidermis also contains dendritic (Langerhans) cells, which are involved in the immune system, and basal cells found at the bottom of the layer. The epidermis also includes squamous cells. The epidermal and dermal layers also contain stem cells and hair follicles. In mammals, melanocytes are also distributed in the brain, eye, ear, and heart, among other tissues.

The skin cells as described are susceptible to UV light-induced damage, DNA damage, and carcinogenesis. Also, normal aging contributes to formation of wrinkles, age spots, loss of skin elasticity, and other signs of aging including superficial wrinkles, a coarse deep wrinkle, enlarged pores, photodamage, scaliness, flakiness, dryness, sagging in skin, puffiness in skin around eye, puffiness in skin around jowl, loss of skin firmness, loss of skin tightness, loss of barrier function, loss of skin recoil from deformation, discoloration, blotching, sallowness, hyperpigmentation, keratosis, hyperkeratinization, elastosis or collagen breakdown, and cellulite, or combinations thereof.

Therefore, in an embodiment, NR, or salts thereof, may be used as follows: to improve the signs of aging including superficial wrinkles, a coarse deep wrinkle, enlarged pores, age spots, photodamage, scaliness, flakiness, dryness, sagging in skin, puffiness in skin around eye, puffiness in skin around jowl, loss of skin elasticity, loss of skin firmness, loss of skin tightness, loss of barrier function, loss of skin recoil from deformation, discoloration, blotching, sallowness, hyperpigmentation, keratosis, hyperkeratinization, elastosis or collagen breakdown, and cellulite, or combinations thereof.

NR, or salts thereof, may be used in combination with one or more stilbenoids. An exemplary stilbenoid compound is pterostilbene (3,5-dimethoxy-4'-hydroxy-trans-stilbene), an orally bioavailable compound with a half life $t_{1/2}$ of about 105 minutes in blood. Pterostilbene is a useful compound for treatment of skin conditions in combination with nicotinamide riboside, or salts thereof.

Optionally, NR, or salts thereof, may be used in combination with pterostilbene, in further combination with curcumin.

Optionally, NR, or salts thereof, may be used in combination with one or more compounds including peptides, retinols, salicylic acid, benzoyl peroxide, vitamin C (L-ascorbic acid), anthocyanins, or combinations thereof. One useful anthocyanin is cyanidin-3-glucoside ("C3 G").

The cosmetic or cosmeceutical compositions of the present invention may be administered in combination with a nutraceutically acceptable carrier. The active ingredients in such formulations may comprise from 1% by weight to 99% by weight, or alternatively, 0.1% by weight to 99.9% by weight. "Nutraceutically acceptable carrier" means any carrier, diluent or excipient that is compatible with the other ingredients of the formulation and not deleterious to the user. Useful excipients include microcrystalline cellulose, magnesium stearate, calcium stearate, any acceptable sugar (e.g., mannitol, xylitol), and for cosmetic use an oil-base is preferred.

The topical pharmaceutical compositions of the present invention may be administered in combination with a pharmaceutically acceptable carrier. The active ingredients in such formulations may comprise from 1% by weight to 99% by weight, or alternatively, 0.1% by weight to 99.9% by weight. "Pharmaceutically acceptable carrier" means any carrier, diluent or excipient that is compatible with the other ingredients of the formulation and not deleterious to the user.

In accordance with certain embodiments, the cosmetic and/or topical pharmaceutical compositions disclosed herein can be provided in the form of an ointment, cream, lotion, gel or other transdermal delivery systems as described in L. V. Allen, Jr., et al., *Ansel's Pharmaceutical Dosage Forms and Drug Delivery Systems*, $9^{th}$ Ed., pp. 272-293 (Philadelphia, Pa.: Lippincott Williams & Wilkins, 2011) which is incorporated herein by reference.

Ointments, as used herein, refer to semi-solid preparations including an ointment base having one or more active ingredients incorporated or fused (i.e., melted together with other components of the formulation and cooled with constant stirring to form a congealed preparation) therein. The ointment base may be in the form of: an oleaginous or hydrocarbon base (e.g., petrolatum or a petrolatum/wax combination); an absorption base which permits the incorporation of aqueous solution resulting in the formation of a water-in-oil emulsion (e.g., hydrophilic petrolatum) or which is a water-in-oil emulsion that permits the incorporation of additional quantities of aqueous solutions (e.g., lanolin); a water-removable base which are oil-in-water emulsions that may be diluted with water or aqueous solutions (e.g., hydrophilic ointment, USP); or a water-soluble base that do not contain oleaginous components (e.g., polyethylene glycol (PEG) formulations which combine PEGs having an average molecular below 600 with a PEG having an average molecular weight above 1,000); and the like.

Creams, as used herein, refer to semisolid preparations containing one or more active or medicinal agent dissolved or dispersed in either a water-in-oil emulsion or an oil-in-water emulsion or in another type of water-washable base. Generally, creams are differentiated from ointments by the ease with which they are applied/spread onto a surface such as the skin and the ease with which they are removed from a treated surface.

Lotions, as used herein, refer to suspensions of solid materials in an aqueous vehicle. Generally, lotions have a non-greasy character and increased spreadability over large areas of the skin than ointments, creams, and gels.

Gels, as used herein, refer to semisolid systems including a dispersion of small and/or large molecules in an aqueous liquid vehicle which is rendered jellylike by the addition of a gelling agent. Suitable gelling agents include, but are not limited to, synthetic macromolecules (e.g., carbomer polymers), cellulose derivatives (e.g., carboxymethylcellulose and/or hydroxypropyl methylcellulose), and natural gums (e.g., tragacanth gum, carrageenan, and the like). Gel preparations may be in the form of a single-phase gel in which the active or medicinal ingredients are uniformly dispersed throughout the liquid vehicle without visible boundaries or a two-phase gel wherein flocculants or small distinct particles of the active or medicinal ingredient are dispersed within the liquid vehicle.

Transdermal preparations may be formed from an ointment, cream, or gel that has been combined with a penetration enhancer and are designed to deliver an active or medicinal ingredient systemically. Penetration enhancers include, for example, dimethyl sulfoxide, ethanol, propylene glycol, glycerin, PEG, urea, dimethyl acetamide, sodium lauryl sulfate, poloxamers, Spans, Tweens, lecithin, and/or terpenes amongst others.

Other suitable semi-solid forms for use as cosmetic and/or topical pharmaceutical compositions include pastes (preparations containing a larger proportion of solid material rendering them stiffer than ointments) and glycerogelatins (plastic masses containing gelatin, glycerin, water, and an active or medicinal ingredient).

In other embodiments the topical and/or cosmetic compositions can be prepared in accordance with dosage forms as described in *Sample Preparation of Pharmaceutical Dosage Forms*, B. Nickerson, Ed. (New York: Springer, 2011) herein incorporated by reference.

Pterostilbene can be provided in daily topical dosages of from about 10 mg to about 250 mg, in a human patient, for example. Another suitable topical dosage range is from about 50 mg to about 150 mg daily. Another suitable topical dosage range is from about 50 mg to about 100 mg daily. A particularly suitable dosage is about 100 mg administered daily.

Routes of Administration

The compounds may be administered by any route, including but not limited to oral, sublingual, buccal, ocular, pulmonary, rectal, and parenteral administration, or as an oral or nasal spray (e.g. inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the instillation of NR in the body of the patient in a controlled formulation, with systemic or local release of the drug to occur at a later time. For example, the drug may be localized in a depot for controlled release to the circulation.

The methods described above may be further understood in connection with the following Examples. In each of the examples, it is contemplated that NR, or a salt thereof, may be used.

Example 1

In one embodiment, NR is used as vehicle for transdermal delivery of compounds and/or pharmaceutical products.

In another embodiment, NR is used as follows: to improve the signs of aging including superficial wrinkles, a coarse deep wrinkle, enlarged pores, age spots, photodamage, scaliness, flakiness, dryness, sagging in skin, puffiness in skin around eye, puffiness in skin around jowl, loss of skin elasticity, loss of skin firmness, loss of skin tightness, loss of barrier function, loss of skin recoil from deformation, discoloration, blotching, sallowness, hyperpigmentation, keratosis, hyperkeratinization, elastosis or collagen breakdown, and cellulite, or combinations thereof.

In another embodiment, NR is used in a method for treating skin damage including rosacea, dermatitis, psoriasis, acne, and UV induced damage (including, for example, sunburn), or combinations thereof.

In another embodiment, NR may be used to reduce the effects of oxidative stress to help prevent the signs of aging.

Example 2

In an embodiment, NR is used in combination with pterostilbene, optionally in further combination with curcumin.

In this example, the NR containing combination functions as a UV induced inflammatory modulator impacting signs of aging and damage from, for example, UV/radiation including skin lightening, inflammation, and redness from sun burn.

Further, in another embodiment, the NR containing combination may be used in treating redness and inflammation associated with the following: acne, rosacea, psoriasis, radiation dermatosis, and wound healing.

In another embodiment, the NR containing combination is used as follows: to improve the signs of aging including superficial wrinkles, a coarse deep wrinkle, enlarged pores, age spots, photodamage, scaliness, flakiness, dryness, sagging in skin, puffiness in skin around eye, puffiness in skin around jowl, loss of skin elasticity, loss of skin firmness, loss of skin tightness, loss of barrier function, loss of skin recoil from deformation, discoloration, blotching, sallowness, hyperpigmentation, keratosis, hyperkeratinization, and elastosis or collagen breakdown, or combinations thereof.

In another embodiment, the NR containing combination is used as follows: to repair DNA in skin, improve DNA repair in skin, and/or potentiate improve DNA-repair processes.

Example 3

In an embodiment, NR is used in combination with one or more stilbenoids (i.e., stilbene compounds). Exemplary stilbenoids are discussed in US2009/0069444 to Joseph et al., albeit for a different use (herein incorporated by reference).

In this example, the NR containing combination with one or more stilbenoids functions as a UV induced inflammatory modulator impacting signs of aging and damage from, for example, UV/radiation including skin lightening, inflammation, acne, and rosacea.

In another embodiment, the NR containing combination with one or more stilbenoids is used as follows: to improve the signs of aging including superficial wrinkles, a coarse deep wrinkle, enlarged pores, age spots, photodamage, scaliness, flakiness, dryness, sagging in skin, puffiness in skin around eye, puffiness in skin around jowl, loss of skin elasticity, loss of skin firmness, loss of skin tightness, loss of barrier function, loss of skin recoil from deformation, discoloration, blotching, sallowness, hyperpigmentation, keratosis, hyperkeratinization, and elastosis or collagen breakdown, or combinations thereof.

In another embodiment, the NR containing combination with one or more stilbenoids is used as follows: to repair DNA in skin, improve DNA repair in skin, and/or potentiate improve DNA-repair processes.

Example 4

In one embodiment, NR is used in combination with one or more peptides to improve transdermal delivery of compounds and/or pharmaceutical products or preparations.

Example 5

In one embodiment, NR is used in combination with one or more of retinols, salicylic acid, benzoyl peroxide, or vitamin C (L-ascorbic acid), for treating skin conditions selected from acne, rosacea, keratosis, psoriasis, dermatitis, and the like.

In the following protocols, NR is used as a chloride salt (NIAGEN™).

Example A

NR Treatment Preventing Oxidative Damage in Human Skin Cells.

A431 human epidermoid cells (ATCC #CRL1555) were grown in DMEM media supplemented with 10% FBS and 1% PenStrep in T75 flasks based on culture recommendations. The media was replaced every two-three days till >80% confluency was attained. The cells were trypsinized with 0.25% trypsin EDTA solution for 2-3 minutes until the cells were dislodged. The cells were sub-cultured in a ratio of 1:3 for further growth and scale-up for the assay. The cells were trypsinized and counted to a density of 5,000 or 15,000 cells and seeded in 1004, media/well in 96-well clear bottom black plates. The outer wells at the periphery of the plates were left unseeded and were instead filled with media to reduce the edge effect during incubation. The plates were incubated overnight in a humidified incubator at 37° C./5% $CO_2$ to confirm that the cells were attached. The Nicotinamide Riboside chloride (NR chloride) was added at indicated final assay concentrations in the media either under pre-treatment for 24 h (without hydrogen peroxide) or along with 1 mM hydrogen peroxide for an incubation of 20 h in a humidified incubator at 37° C./5% $CO_2$ either with media replenishment at 8 h or under growth synchronized conditions using 1% FBS. Each concentration was tested in 6 replicates. Appropriate controls: cells without compound and hydrogen peroxide (no cytotoxicity; negative control), cells without compound but in the presence of 1 mM hydrogen peroxide (positive control), wells with alamar blue alone (blank) were kept in each assay.

Cell viability was graphed and data was represented as percent cytotoxicity for 1 mM $H_2O_2$ under a given assay condition with respect to negative (untreated control) cells or percent cytoprotection in the presence of the test compound calculated with respect to positive (1 mM H2O2) control.

For growth synchronized samples, comparison of positive control to negative control showed a 75% cytotoxicity after $H_2O_2$ treatment, while treatment with NR chloride at 0.2 mM, 1 mM, and 5 mM showed 2%, 15%, and 38% cytoprotection, respectively, compared to controls (see FIG. 1).

Figure 2:
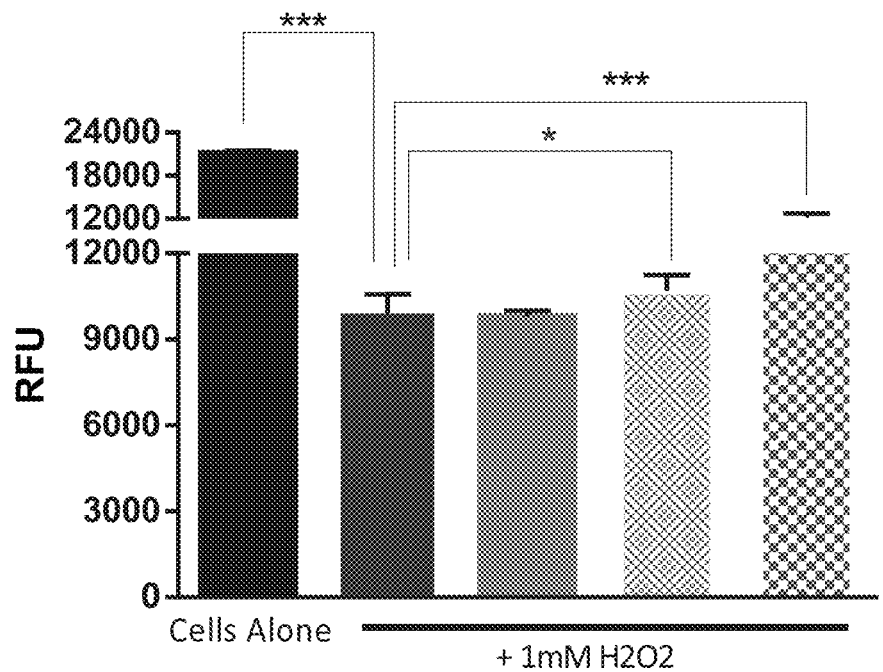
FIG. 2 depicts the experiment of FIG. 1 incubated with 1 mM $H_2O_2$ under normal growth conditions (10% FBS); control, +0.04 mM NR; +0.2 mM NR; and +1 mM NR.

For normal growth samples, comparison of positive control to negative control showed a 53% cytotoxicity after $H_2O_2$ treatment, while treatment with NR chloride at 0.04 mM, 0.2 mM, and 1 mM showed −1%, 8%, and 23% cytoprotection, respectively, compared to controls (see FIG. 2).

In conclusion, it was observed that the presence of NR reduced oxidative damage-mediated cell death by 10-40%, even in growth arrested condition. It is further expected that treatment with NR chloride will be effective to reduce oxidative damage-mediated cell death at least about 10%, or greater.

Example B

NR Treatment Preventing Harmful UV-C-Mediated Damage in Human Skin Cells.

The A431 cell line was seeded in 6-wells plate at a seeding density of $4\times10^5$ cells/well in 2 ml of culture media containing 10% FBS. The cells were left untreated as a control or treated with different concentrations of NR chloride in the media (5 mM and 1 mM) for 2 h under a fully humidified atmosphere containing 5% $CO_2$ at 37° C. After incubation, culture media was replaced by PBS and cells were exposed to 10 $J/m^2$ UVC irradiation. Plates were harvested along with respective controls immediately after UVC exposure (Negative Control was cells without UV-C exposure while Positive Control was untreated Cells with UV-C exposure). DNA from cells in each condition was extracted and quantified by NanoDrop. DNA samples were then added in the ELISA plate at 100 ng/well conc. and amount of cyclobutane pyrimidine dimer (CPD) was estimated in the DNA samples using CPD-DNA estimation kits (OxiSelect™, Cell Biolabs, Inc., San Diego, USA) as per manufacturer's protocol.

Figure 3:
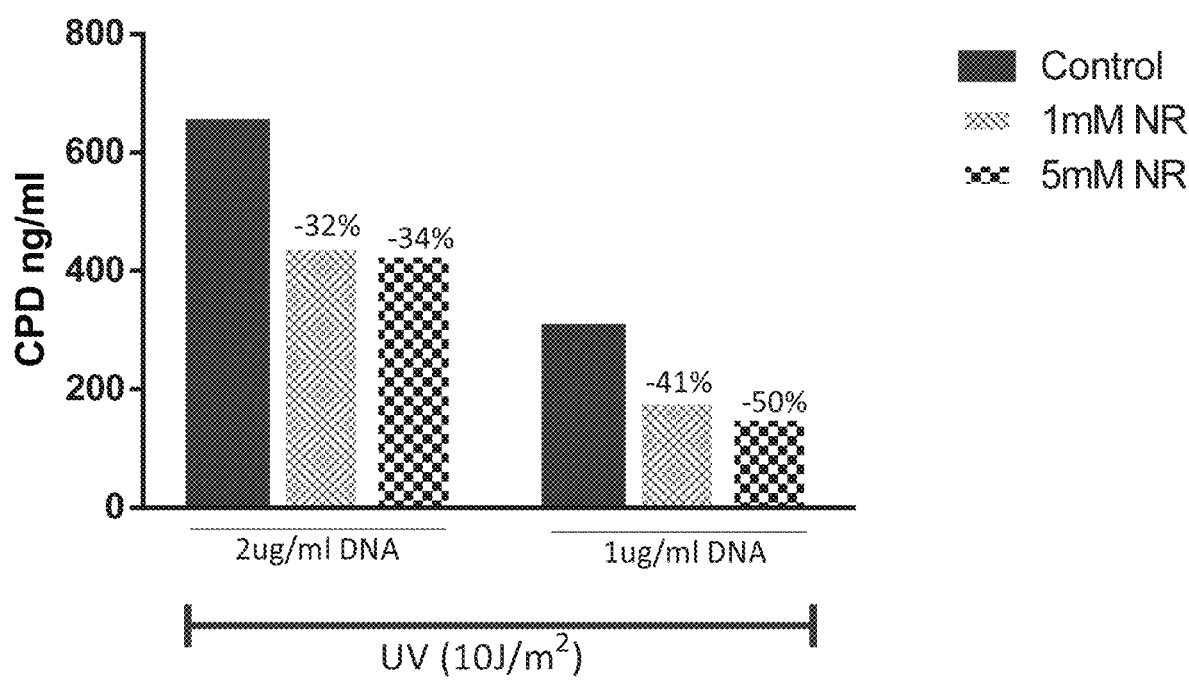
FIG. 3 depicts a UV damage assay of human epidermoid A431 cells pre-treated with cell media (control); +1 mM NR; and +5 mM NR; then all samples exposed to UV-C radiation at 10 $J/m^2$. UV-induced DNA damage is reflected in cyclobutane pyrimidine dimer (CPD) level.

UV-induced DNA damage is reflected in cyclobutane pyrimidine dimer (CPD) level: 1.2 µg/ml DNA control; +1 mM NR chloride (−32% vs. control); +5 mM NR chloride (−34% vs. control); 2.1 µg/ml DNA control; +1 mM NR chloride (−41% vs. control); +5 mM NR chloride (−50% vs. control); see FIG. 3.

In conclusion, it was observed that NR was efficacious in reducing the amount of CPDs in the range of 32% to 50% compared to untreated UV-exposed control. It is further expected that treatment with NR chloride will be effective to reduce levels of CPDs at least about 10%, or greater.

Example C1 (Control Experiment)

NR Treatment Promoting Cell Growth and Migration in Mouse Skin Cells.

NIH 3T3 fibroblasts were obtained from ATCC (#CRL-1658™) and cultured in Dulbecco's modified Eagle's medium (DMEM) supplemented with 10% fetal bovine serum (FBS), 4 mM L-glutamine, 1% penicillin/streptomycin under a fully humidified atmosphere containing 5% $CO_2$ at 37° C. For experiments, cells were collected from sub-confluent monolayers with trypsin/EDTA. Cell viability was higher as 95% using trypan blue dye exclusion staining. The study was carried out using cells from passages 4-7 in DMEM medium containing 1% FBS. Untreated cells (1% FBS) were used as negative controls. The effect of nicotinamide riboside chloride (NR chloride) on wound closure in NIH 3T3 fibroblasts was investigated.

Cell viability was determined by cell titer blue (Promega), wound closure by CytoSelect™ Wound Healing Assay Kit (Cell Biolabs, Inc., San Diego, USA). All conditions were performed in three independent, controlled experiments. In brief, NIH 3T3 fibroblasts ($2.5\times10^5$/500 µl) in DMEM containing 10% FBS were seeded into 24-well tissue culture plates containing treated inserts in each well with their wound field aligned in the same orientation for 24 h allowing the cells to adhere and reach ~70-80% confluence. After 24 h, the inserts from the wells were removed and the medium was carefully aspirated without disturbing the cells, followed by washing the wells with test medium (DMEM containing 1% FBS) to remove dead cells and debris. Post washing, the cells were treated with different concentrations of test compounds in a media containing 1% FBS for further 24 hours while the migration of NIH3T3 cells in the wound field was studied by visual examination under light microscope according to manufacturer's instructions. Representative images focused on the center of the wound field were photographed. Microscopic imaging of wound closure was analyzed using "Image J" software. The effect of test compound on wound closure was compared to 1% FBS control well at "Zero min." and at 24 h post compound treatment. DMEM with 5% FBS was used as a positive control. Density of cells in wells without created wound area (confluent area) was used as 100% wound closure. Apart from microscopic observations, data was analyzed for the determination of total surface area of the defined wound area using "Image J" software. Surface area of the migrated cells into the wound area was calculated by subtracting surface area after 24 hour from total surface area of the wound at "0" hour. Percent (%) closure was calculated as the ratio of migrated cell surface area to total surface area while the gap closure (%) was determined by subtracting percent closure in the presence of control untreated sample from treated test sample.

Figure 4A:
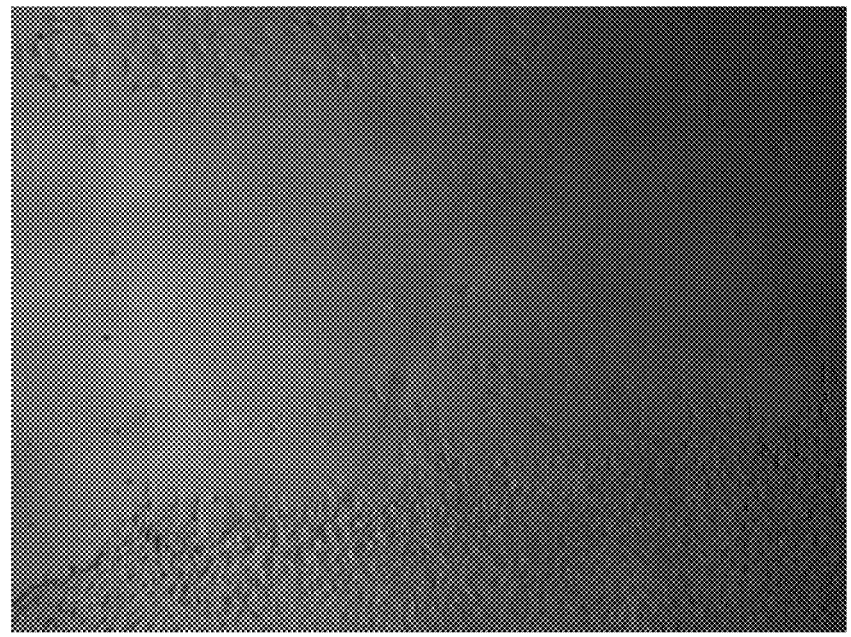
FIG. 4A is a photomicrograph at 40× magnification showing a first scratch wound healing assay of mouse NIH 3T3 fibroblast cells incubated with 1% FBS (0 hr).
Figure 4B:
FIG. 4B is a photomicrograph at 40× magnification showing the scratch wound healing assay of FIG. 4A incubated with 1% FBS (24 hr) demonstrating gap closure via cell migration.
Figure 5A:
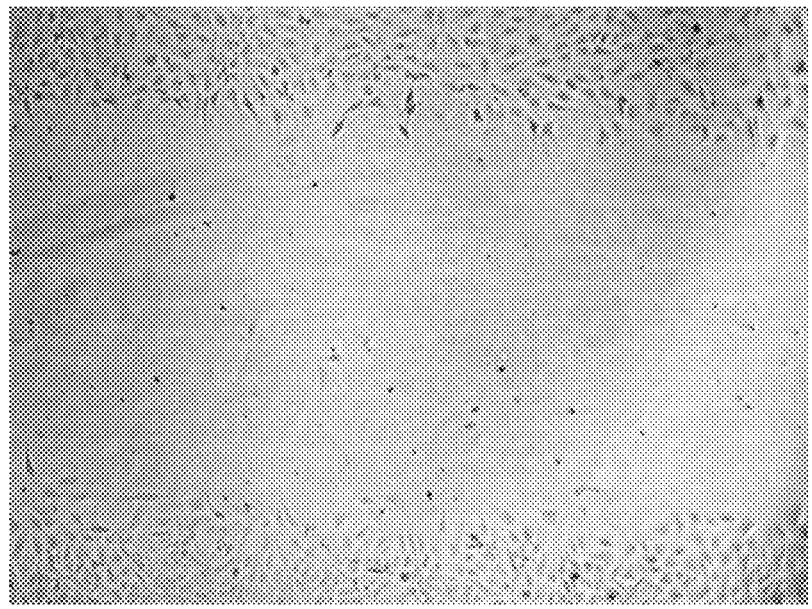
FIG. 5A is a photomicrograph at 40× magnification showing the first scratch wound healing assay of mouse NIH 3T3 fibroblast cells incubated with 5% FBS control (0 hr).
Figure 5B:
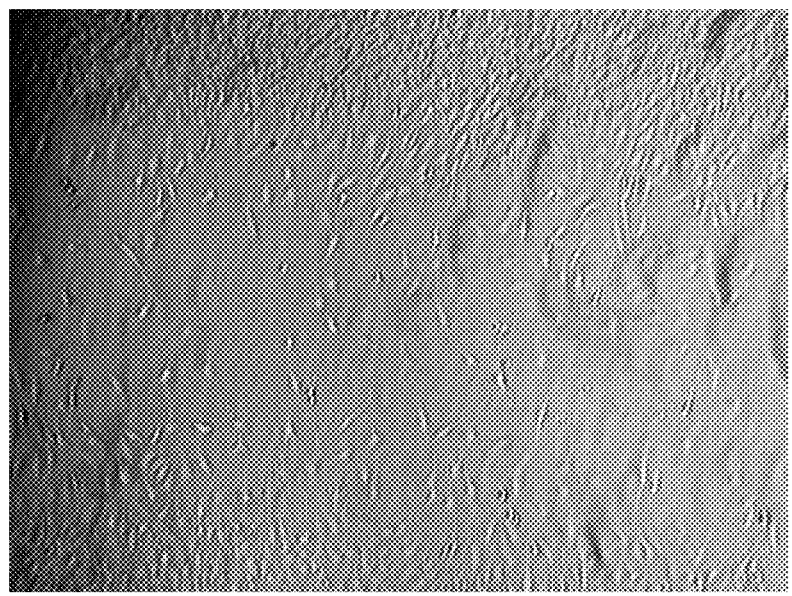
FIG. 5B is a photomicrograph at 40× magnification showing the scratch wound healing assay of FIG. 5A incubated with 5% FBS control (24 hr) demonstrating gap closure via cell migration.

It was observed that gap closure was 51% in the presence of 5% FBS compared to 20% in the presence of 1% FBS post 24 hour incubation, as shown in FIGS. 5 and 4, respectively.

Example C2 (NR Dose Response)

NR Treatment Promoting Cell Growth and Migration in Mouse Skin Cells.

Using the same experimental conditions as described in EXAMPLE C1, The effect of Nicotinamide riboside chloride in the media (1 mM and 0.2 mM) on wound closure was investigated with CytoSelect™ Wound Healing Assay Kit.

Figure 6A:
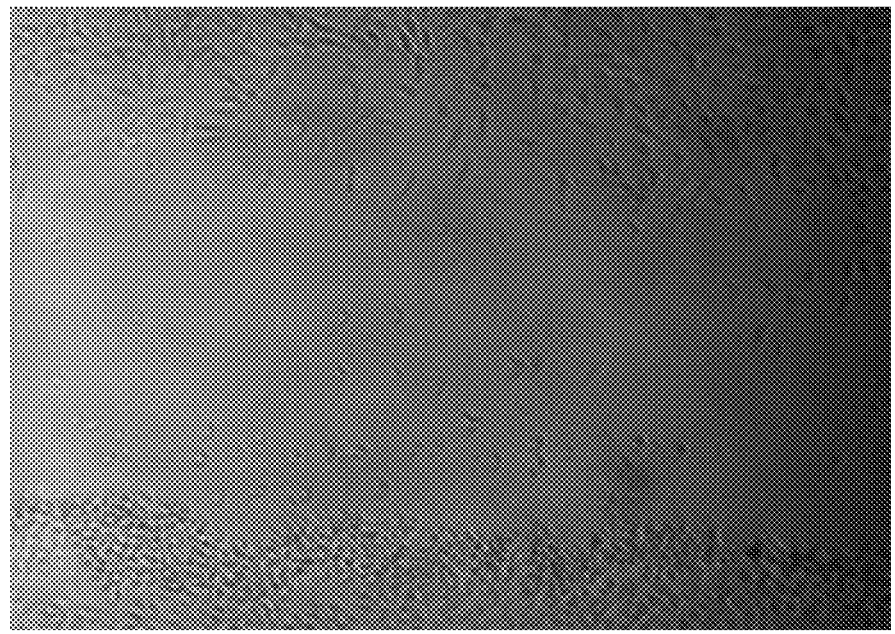
FIG. 6A is a photomicrograph at 40× magnification showing a second scratch wound healing assay of mouse NIH 3T3 fibroblast cells incubated with 1% FBS+1 mM NR (0 hr).
Figure 6B:
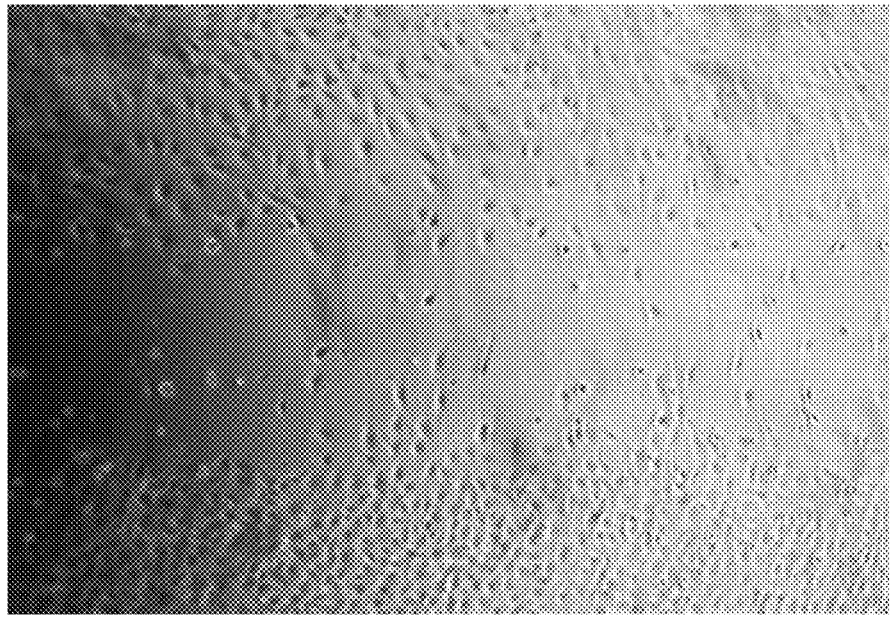
FIG. 6B is a photomicrograph at 40× magnification showing the scratch wound healing assay of FIG. 6A incubated with 1% FBS+1 mM NR (24 hr) demonstrating gap closure via cell migration.

It was observed that gap closure was 46% in the presence of 1 mM NR chloride+1% FBS compared to 20% in the presence of 1% FBS alone post 24 hour incubation (Example C1); see FIG. 6. Thus, gap closure indicative of cell motility in the presence of NR (at 1% FBS) was comparable to 5% FBS as control in Example C1. Furthermore, 13% gap closure was observed in the presence of 0.2 mM NR (+1% FBS), demonstrating a dose response effect.

Mammalian tissue wounds undergo a complex and ordered series of events to repair tissue. Two key components of that repair are cell motility and proliferation. The data presented here clearly demonstrate that NR promotes cell motility and proliferation of mammalian skin cells into a "wound".

Example D

NR Treatment Preventing Harmful UV-Mediated Damage in Human Skin Cells.

In this example nicotinamide riboside (NR) is used to help maintain healthy barrier function of skin. Barrier function is the most important function of skin. Skin is the human body's first and best defense against environmental exposures including solar ultraviolet (UV) radiation. Exposure to UV light is a key factor in the development of many skin disorders. A central component UV-mediated damage to skin is loss of barrier function.

Application of topical NR at therapeutic doses as described herein is expected to prevent UV-mediated loss of barrier function. One way in which NR will prevent UV-mediated loss of skin barrier function is by preventing the known UV-mediated increase in transepidermal water loss (TEWL). In addition it is anticipated that oral administration of NR will be efficacious in maintenance of healthy barrier function of the skin.

For example, skin barrier dysfunction can be directly assessed by measuring Transepidermal Water Loss (TEWL), which is a measure of skin hydration (Oba, C., et al., "Collagen hydrolysate intake improves the loss of epidermal barrier function and skin elasticity induced by UVB irradiation in hairless mice," *Photodermatol. Photoimmunol. Photomed.* (2013) 29: 204-11; and references cited therein; Jiang, S. J., et al., "Ultraviolet B-induced alterations of the skin barrier and epidermal calcium gradient," *Exp. Dermatol.* (2007) 16: 985-992); and Haratake, A., et al., "UVB-induced alterations in permeability barrier function: roles for epidermal hyperproliferation and thymocyte-mediated response" *J. Invest. Dermatol.* (1997) 108: 769-775).

The use of the terms "a," "an," "the," and similar referents in the context of describing the presently claimed invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approx. ±10%; in other embodiments the values may range in value either above or below the stated value in a range of approx. ±5%; in other embodiments the values may range in value either above or below the stated value in a range of approx. ±2%; in other embodiments the values may range in value either above or below the stated value in a range of approx. ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A chemoprotective method for treating UV-mediated DNA damage in the skin of an individual comprising topically administering to the individual in need of such treatment a therapeutically effective amount of the compound nicotinamide riboside, or a salt thereof.

2. The chemoprotective method of claim 1, wherein the individual is a human.

3. The chemoprotective method of claim 2, wherein the nicotinamide riboside compound, or a salt thereof, is provided in a composition comprising a pharmaceutically acceptable carrier.

4. The chemoprotective method of claim 3, wherein the nicotinamide riboside compound is a salt selected from the group consisting of fluoride, chloride, bromide, iodide, formate, acetate, ascorbate, benzoate, carbonate, citrate, carbamate, gluconate, lactate, methyl bromide, methyl sulfate, nitrate, phosphate, diphosphate, succinate, sulfate, and trifluoroacetate.

5. The chemoprotective method of claim 4, wherein the nicotinamide riboside compound is a chloride salt.

6. The chemoprotective method of claim 3, wherein the therapeutically effective amount of nicotinamide riboside compound, or a salt thereof, for a total dose is in a range of about 0.01% by weight to about 50% by weight based on the total weight of the composition.

7. The chemoprotective method of claim 3, wherein the therapeutically effective amount of nicotinamide riboside compound, or a salt thereof, for a total dose is in a range of about 0.1% by weight to about 10% by weight based on the total weight of the composition.

8. The chemoprotective method of claim 1, wherein DNA damage indicated by formation of cyclobutane-pyrimidine dimers (CPDs) or 6-4 photoproducts (64 pps) is decreased by greater than about 10%.

9. A cytoprotective method for treating oxidative damage in the skin of an individual comprising topically administering to the individual in need of such treatment a therapeutically effective amount of the compound nicotinamide riboside, or a salt thereof.

10. The cytoprotective method of claim 9, wherein the individual is a human.

11. The cytoprotective method of claim 10, wherein the nicotinamide riboside compound, or a salt thereof, is provided in a composition comprising a pharmaceutically acceptable carrier.

12. The cytoprotective method of claim 11, wherein the nicotinamide riboside compound is a salt selected from the group consisting of fluoride, chloride, bromide, iodide, formate, acetate, ascorbate, benzoate, carbonate, citrate, carbamate, gluconate, lactate, methyl bromide, methyl sulfate, nitrate, phosphate, diphosphate, succinate, sulfate, and trifluoroacetate.

13. The cytoprotective method of claim 12, wherein the nicotinamide riboside compound is a chloride salt.

14. The cytoprotective method of claim 11, wherein the therapeutically effective amount of nicotinamide riboside compound, or a salt thereof, for a total dose is in a range of about 0.01% by weight to about 50% by weight based on the total weight of the composition.

15. The cytoprotective method of claim 11, wherein the therapeutically effective amount of nicotinamide riboside compound, or a salt thereof, for a total dose is in a range of about 0.1% by weight to about 10% by weight based on the total weight of the composition.

16. The cytoprotective method of claim 9, wherein cell death is decreased by greater than about 10%.

* * * * *